United States Patent
Bonutti

(12) 
(10) Patent No.: US 6,990,982 B1
(45) Date of Patent: Jan. 31, 2006

(54) METHOD FOR HARVESTING AND PROCESSING CELLS FROM TISSUE FRAGMENTS

(75) Inventor: Peter M. Bonutti, Watson, IL (US)

(73) Assignee: Bonutti IP, LLC, Effingham, IL (US)

( * ) Notice: Subject to any disclaimer, the term of this patent is extended or adjusted under 35 U.S.C. 154(b) by 0 days.

(21) Appl. No.: 10/386,856

(22) Filed: Mar. 12, 2003

Related U.S. Application Data

(60) Continuation of application No. 10/044,388, filed on Jan. 11, 2002, now Pat. No. 6,543,455, which is a division of application No. 09/483,676, filed on Jan. 14, 2000, now Pat. No. 6,468,289, which is a continuation of application No. 09/323,326, filed on Jun. 1, 1999, now Pat. No. 6,174,313, which is a continuation of application No. 08/834,835, filed on Apr. 11, 1997, now Pat. No. 5,935,131, which is a division of application No. 08/695,274, filed on Aug. 9, 1996, now Pat. No. 5,694,951, which is a division of application No. 08/353,494, filed on Dec. 9, 1994, now Pat. No. 5,577,517, which is a division of application No. 08/134,914, filed on Oct. 12, 1993, now Pat. No. 5,403,317, which is a division of application No. 07/545,908, filed on Jun. 28, 1990, now Pat. No. 5,269,785.

(51) Int. Cl.
*A61B 19/00* (2006.01)
(52) U.S. Cl. .................................... 128/898; 623/23.72
(58) Field of Classification Search ................ 128/898; 623/23.72

See application file for complete search history.

(56) References Cited

U.S. PATENT DOCUMENTS 1,959,615 A  5/1934  Derrah
2,433,815 A  12/1947  Laforge (Continued)

FOREIGN PATENT DOCUMENTS

DE  3707787 A1  9/1988

(Continued)

OTHER PUBLICATIONS

Brian A. Naughton, Hematopoiesis on Nylon Mesh Templates, vol. 18, Nos. 3 & 4, (1987), pp. 219-250.

(Continued)

*Primary Examiner*—Gary Jackson
(74) *Attorney, Agent, or Firm*—Fleit Kain Gibbons Gutman Bongini & Bianco; Paul D. Bianco; Martin Fleit

(57) ABSTRACT

A percutaneous tissue removal apparatus having a flexible drill shaft, a cutting tip mounted on the shaft a power source for transmitting motion to the shaft to move the cutting tip against tissue and a suction source for removing tissue fragments along the shaft to a location outside the tissue mass while cutting. The apparatus may include a container for collecting one or more selected components of the harvested tissue fragments for implantation of the fragments preferably into the body of the patient from whom they were removed. Where the tissue to be cut is bone, a cutting tip is preferably made of a polymeric material which is softer than the cortical portion of the bone, although the cutting tip may be made of a ceramic or a composite material. A second flexible shaft may be provided either within or about the flexible drill shaft.

19 Claims, 5 Drawing Sheets

U.S. PATENT DOCUMENTS

| | | |
|---|---|---|
| 2,526,662 A | 10/1950 | Hipp et al. |
| 2,621,145 A | 12/1952 | Sano |
| 2,724,326 A | 11/1955 | Long |
| 2,955,530 A | 10/1960 | Nilo |
| 3,048,522 A | 8/1962 | Velley |
| 3,108,357 A | 10/1963 | Liebig |
| 3,514,791 A | 6/1970 | Sparks |
| 3,554,192 A | 1/1971 | Isberner |
| 3,593,709 A | 7/1971 | Halloran |
| 3,613,497 A | 10/1971 | Heldermann |
| 3,670,732 A | 6/1972 | Robinson |
| 3,721,244 A | 3/1973 | Elmaleh |
| 3,769,980 A | 11/1973 | Karman |
| 3,804,089 A | 4/1974 | Bridgman |
| 3,812,855 A | 5/1974 | Banko |
| 3,874,264 A | 4/1975 | Polos |
| 3,894,530 A | 7/1975 | Dardik |
| 3,939,835 A | 2/1976 | Bridgman |
| 3,945,375 A | 3/1976 | Banko |
| 4,092,113 A | 5/1978 | Hardy |
| 4,122,605 A | 10/1978 | Hirabayashi |
| 4,142,517 A | 3/1979 | Stavropoulos et al. |
| 4,186,448 A | 2/1980 | Brekke |
| 4,191,747 A | 3/1980 | Scheicher |
| 4,210,580 A | 7/1980 | Amrani |
| 4,243,048 A | 1/1981 | Griffin |
| 4,265,231 A | 5/1981 | Scheller, Jr. et al. |
| 4,274,414 A | 6/1981 | Johnson |
| 4,298,002 A | 11/1981 | Ronel |
| 4,298,998 A | 11/1981 | Naficy |
| 4,304,178 A | 12/1981 | Haberle |
| 4,352,883 A | 10/1982 | Lim |
| 4,391,909 A | 7/1983 | Lim |
| 4,400,833 A | 8/1983 | Kurland |
| 4,430,760 A | 2/1984 | Smestad |
| 4,442,655 A | 4/1984 | Stroetmann |
| 4,445,509 A | 5/1984 | Auth |
| 4,453,421 A | 6/1984 | Umano |
| 4,466,429 A | 8/1984 | Loscher et al. |
| 4,466,888 A | 8/1984 | Verkaart |
| 4,472,840 A | 9/1984 | Jefferies |
| 4,485,096 A | 11/1984 | Bell |
| 4,501,269 A | 2/1985 | Bagby |
| 4,502,159 A | 3/1985 | Woodroof |
| 4,516,276 A | 5/1985 | Mittelmeier |
| 4,541,423 A | 9/1985 | Barber |
| 4,551,135 A | 11/1985 | Gorman |
| 4,553,272 A | 11/1985 | Mears |
| 4,554,686 A | 11/1985 | Baker |
| 4,562,598 A | 1/1986 | Kranz |
| 4,573,448 A | 3/1986 | Kambin |
| 4,589,414 A | 5/1986 | Yoshida et al. |
| 4,603,694 A | 8/1986 | Wheeler |
| 4,623,553 A | 11/1986 | Ries |
| 4,642,117 A | 2/1987 | Nguyen |
| 4,642,120 A | 2/1987 | Nevo |
| 4,646,736 A | 3/1987 | Auth |
| 4,646,738 A | 3/1987 | Trott |
| 4,649,918 A | 3/1987 | Pegg et al. |
| 4,651,752 A | 3/1987 | Fuerst |
| 4,654,464 A | 3/1987 | Mittelmeier |
| 4,657,548 A | 4/1987 | Nichols |
| 4,678,470 A | 7/1987 | Nashef et al. |
| 4,681,106 A | 7/1987 | Kensev et al. |
| 4,696,667 A | 9/1987 | Masch |
| 4,706,659 A | 11/1987 | Matthews |
| 4,718,916 A | 1/1988 | Morscher |
| 4,721,096 A | 1/1988 | Naughton |
| 4,743,229 A | 5/1988 | Chu |
| 4,743,259 A | 5/1988 | Bolander |
| 4,747,405 A | 5/1988 | Leckrone |
| 4,750,488 A | 6/1988 | Wuchinich |
| 4,751,922 A | 6/1988 | De Pietropolo |
| 4,755,184 A | 7/1988 | Silverberg |
| 4,789,663 A | 12/1988 | Wallace |
| 4,790,819 A | 12/1988 | Li |
| 4,794,854 A | 1/1989 | Swaim |
| 4,795,467 A | 1/1989 | Piez |
| 4,798,213 A | 1/1989 | Doppelt |
| 4,801,299 A | 1/1989 | Brendel |
| 4,828,563 A | 5/1989 | Muller-Lierheim |
| 4,832,683 A | 5/1989 | Idemoto et al. |
| 4,834,757 A | 5/1989 | Brantigan |
| 4,842,517 A | 6/1989 | Kawahara |
| 4,844,064 A | 7/1989 | Thimsen et al. |
| 4,846,791 A | 7/1989 | Hattler |
| 4,846,835 A | 7/1989 | Grande |
| 4,857,045 A | 8/1989 | Rydell |
| 4,863,472 A | 9/1989 | Tormala |
| 4,867,157 A | 9/1989 | McGurk-Burleson et al. |
| 4,883,666 A | 11/1989 | Sadel |
| 4,888,022 A | 12/1989 | Huebsch |
| 4,890,612 A | 1/1990 | Kensey |
| 4,892,552 A | 1/1990 | Ainsworth |
| 4,902,296 A | 2/1990 | Bolander |
| 4,904,259 A * | 2/1990 | Itay .......................... 435/325 |
| 4,932,973 A | 6/1990 | Gendler |
| 4,936,848 A | 6/1990 | Bagby |
| 4,950,296 A | 8/1990 | McIntyre |
| 4,961,740 A | 10/1990 | Ray |
| 4,963,489 A | 10/1990 | Naughton |
| 4,976,682 A | 12/1990 | Lane |
| 4,978,355 A | 12/1990 | Frey |
| 4,984,585 A | 1/1991 | Austad |
| 4,994,067 A | 2/1991 | Summers |
| 5,015,247 A | 5/1991 | Michelson |
| 5,027,827 A | 7/1991 | Cody et al. |
| 5,030,201 A | 7/1991 | Palestrant |
| 5,047,040 A | 9/1991 | Simpson et al. |
| 5,055,198 A | 10/1991 | Shettigar |
| 5,057,120 A | 10/1991 | Farcot |
| 5,059,193 A | 10/1991 | Kuslich |
| 5,061,286 A | 10/1991 | Lyle |
| 5,062,843 A | 11/1991 | Mahony |
| 5,073,373 A | 12/1991 | O'Leary |
| 5,082,670 A | 1/1992 | Gage |
| 5,084,050 A | 1/1992 | Draenert |
| 5,087,260 A | 2/1992 | Fixel |
| 5,098,435 A | 3/1992 | Stednitz |
| 5,100,424 A | 3/1992 | Jang |
| 5,101,720 A | 4/1992 | Bianchi |
| 5,108,438 A | 4/1992 | Stone |
| 5,152,744 A | 10/1992 | Krause |
| 5,152,776 A | 10/1992 | Pinchok |
| 5,162,430 A | 11/1992 | Rhee |
| 5,162,506 A | 11/1992 | Hadden |
| 5,167,239 A | 12/1992 | Cohen et al. |
| 5,171,244 A | 12/1992 | Caspari et al. |
| 5,171,273 A | 12/1992 | Silver |
| 5,185,001 A | 2/1993 | Galanakis |
| 5,188,834 A | 2/1993 | Grimm |
| 5,190,541 A | 3/1993 | Abele |
| 5,192,327 A | 3/1993 | Brantigan |
| 5,204,106 A | 4/1993 | Schepers et al. |
| 5,212,082 A | 5/1993 | Goldstein |
| 5,226,877 A | 7/1993 | Epstein |
| 5,236,456 A | 8/1993 | Oleary |
| 5,240,862 A | 8/1993 | Koenhan |
| 5,246,457 A | 9/1993 | Piez |
| 5,269,785 A | 12/1993 | Bonutti |
| 5,278,201 A | 1/1994 | Dunn |
| 5,284,655 A | 2/1994 | Bogdansky |
| 5,285,795 A | 2/1994 | Ryan |
| 5,298,254 A | 3/1994 | Prewett et al. |

| | | |
|---|---|---|
| 5,329,846 A | 7/1994 | Bonutti |
| 5,355,898 A | 10/1994 | Ripamonti |
| 5,372,138 A | 12/1994 | Crowley et al. |
| 5,390,683 A | 2/1995 | Pishandi |
| 5,401,759 A | 3/1995 | Dunnett |
| 5,403,317 A | 4/1995 | Bonutti |
| 5,443,443 A | 8/1995 | Shiber |
| 5,480,437 A | 1/1996 | Draenert |
| 5,487,897 A | 1/1996 | Polson |
| 5,501,706 A | 3/1996 | Arenberg |
| 5,514,153 A | 5/1996 | Bonutti |
| 5,545,222 A | 8/1996 | Bonutti |
| 5,577,517 A | 11/1996 | Bonutti |
| 5,593,425 A | 1/1997 | Bonutti |
| 5,660,849 A | 8/1997 | Polson |
| 5,662,710 A | 9/1997 | Bonutti |
| 5,694,951 A | 12/1997 | Bonutti |
| 5,713,853 A | 2/1998 | Clark et al. |
| 5,779,728 A | 7/1998 | Lunsford |
| 5,833,692 A | 11/1998 | Cesarini |
| 5,868,749 A | 2/1999 | Reed |
| 5,888,219 A | 3/1999 | Bonutti |
| 5,935,131 A | 8/1999 | Bonutti |
| 5,954,739 A | 9/1999 | Bonutti |
| 5,968,048 A | 10/1999 | Harder |
| 6,132,472 A | 10/2000 | Bonutti |
| 6,156,070 A | 12/2000 | Incavo |
| 6,174,313 B1 | 1/2001 | Bonutti |
| 6,261,295 B1 | 7/2001 | Nicholson |
| 6,312,438 B1 | 11/2001 | Adams |
| 6,325,806 B1 | 12/2001 | Fox |
| 6,358,252 B1 | 3/2002 | Shapira |
| 6,361,565 B1 | 3/2002 | Bonutti |
| 6,409,764 B1 | 6/2002 | White et al. |
| 6,503,277 B2 | 1/2003 | Bonutti |
| RE38,018 E | 3/2003 | Anctil |

FOREIGN PATENT DOCUMENTS

| | | |
|---|---|---|
| EP | 0192576 A1 | 8/1986 |
| FR | 2344267 A1 | 10/1977 |
| WO | WO 88/01517 A1 | 3/1988 |

OTHER PUBLICATIONS

Marcel E. Nimmi, Ectopic Bone Formation Is Enhanced in Senescent Animals Implanted with Embryonic Cells, Clinical Orthopaedic and Related Research 234, (1988), pp. 255-266.

John A. Bierly, Osseous Filtration: An Improved Technique for Bone Implantation, J. Periodontol, Jun. 1974, pp. 414-420.

* cited by examiner

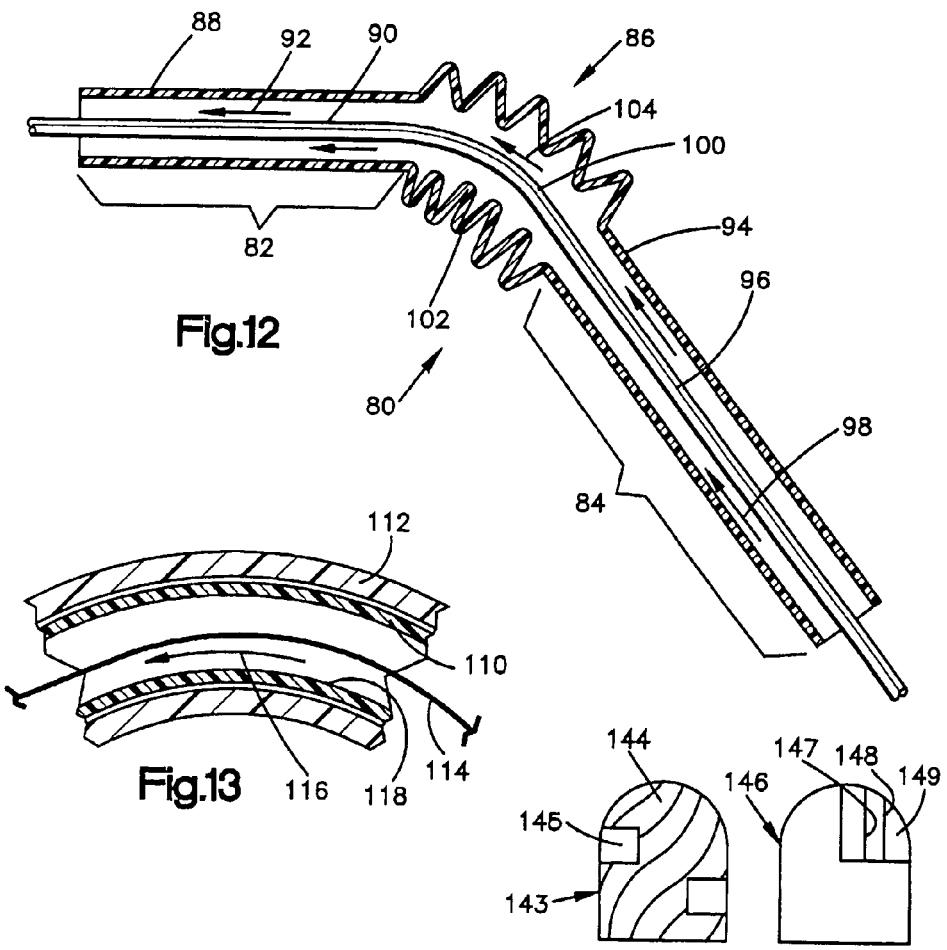
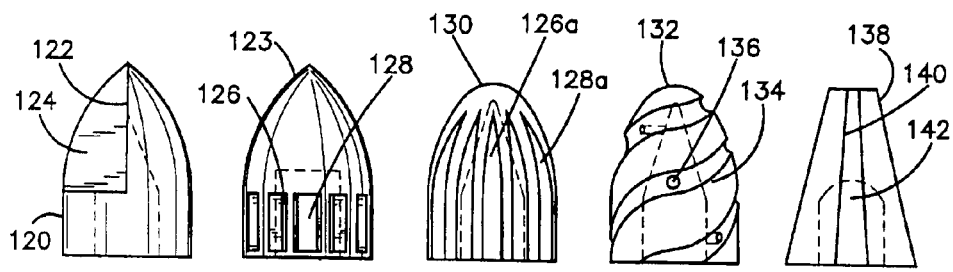

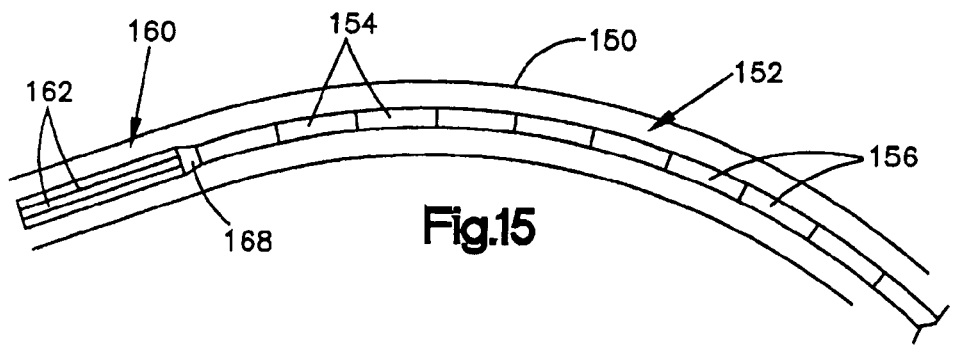
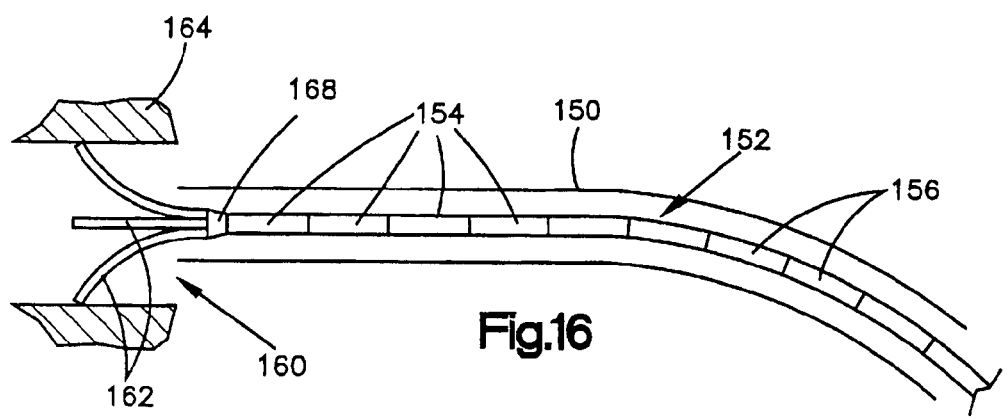
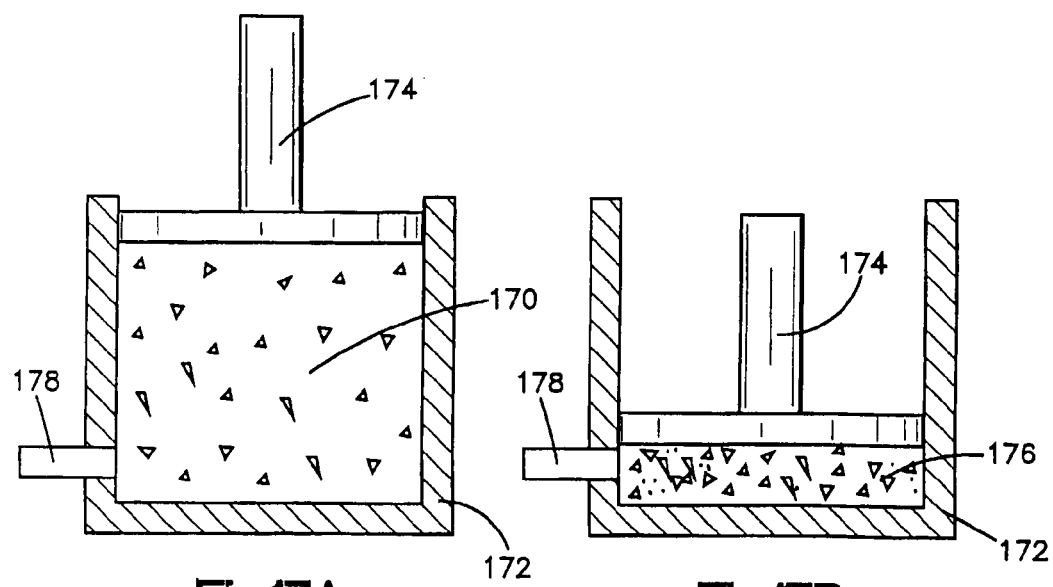

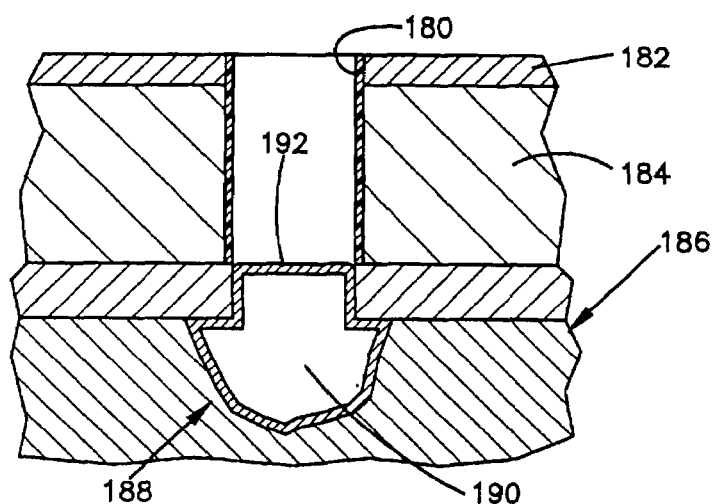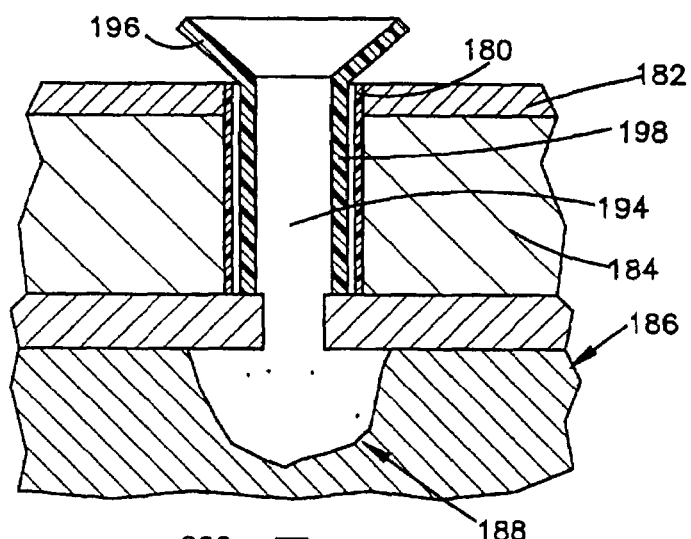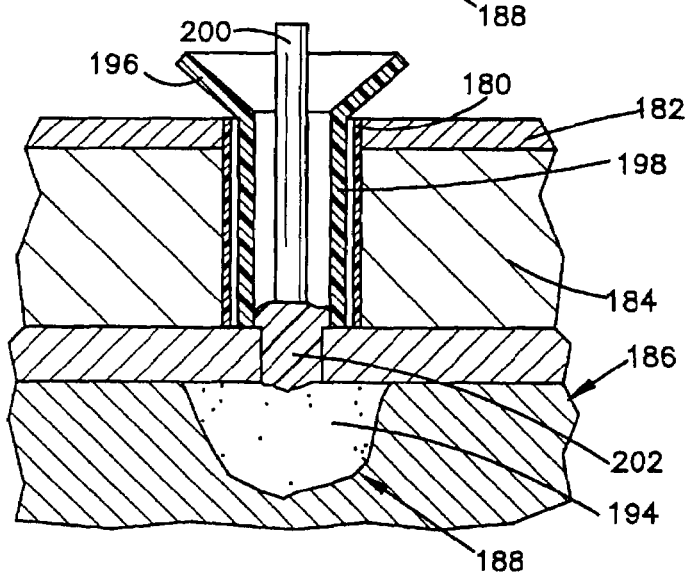

METHOD FOR HARVESTING AND PROCESSING CELLS FROM TISSUE FRAGMENTS

CROSS-REFERENCE TO RELATED APPLICATIONS

This application is a continuation of U.S. patent application Ser. No. 10/044,388, filed Jan. 11, 2002, now U.S. Pat. No. 6,543,455 which in turn is a divisional of U.S. patent application Ser. No. 09/483,676, filed Jan. 14, 2000 now U.S. Pat. No. 6,468,289. The aforementioned application Ser. No. 09/483,676 is itself a continuation of U.S. patent application Ser. No. 09/323,326, filed Jun. 1, 1999 (now U.S. Pat. No. 6,174,313 B1). The aforementioned application Ser. No. 09/323,326 is itself a continuation of U.S. patent application Ser. No. 08/834,835, filed Apr. 11, 1997 (now U.S. Pat. No. 5,935,131). The aforementioned application Ser. No. 08/834,835 is itself a divisional of U.S. patent application Ser. No. 08/695,274, filed Aug. 9, 1996 (now U.S. Pat. No. 5,694,951). The aforementioned application Ser. No. 08/695,274 is itself a divisional of U.S. patent application Ser. No. 08/353,494, filed Dec. 9, 1994 (now U.S. Pat. No. 5,577,517). The aforementioned application Ser. No. 08/353,494 is itself a divisional of U.S. patent application Ser. No. 08/134,914, filed Oct. 12, 1993 (now U.S. Pat. No. 5,403,317). The aforementioned application Ser. No. 08/134,914 is itself a divisional of U.S. patent application Ser. No. 07/545,908, filed Jun. 28, 1990 (now U.S. Pat. No. 5,269,785).

BACKGROUND OF THE INVENTION

1. Technical Field

The present invention relates to the field of tissue removal and tissue grafting. More particularly, the present invention relates to an apparatus and method for the percutaneous cutting and removal of selected portions of tissue from a patient and the possible harvesting and implantation of the tissue portion in the donor.

2. Description of the Prior Art

There are various known methods and apparatus for the cutting and removal of tissue fragments from a human. Each of these, however, suffers from one or more deficiencies.

U.S. Pat. No. 4,832,683 shows an instrument for ultrasonic cutting of bones, with irrigation or suction. However, there is no suction while cutting, no removal of the cut bone or tissue, and no flexibility in the instrument.

U.S. Pat. No. 4,265,231 shows apparatus for drilling a curved hole having a flexible shaft confined in a rigid tubular sheath, but which shows no removal of cut bone or tissue.

U.S. Pat. No. 4,541,423 shows apparatus for drilling a curved hole having a flexible shaft confined in a semi-rigid tubular sheath, but which shows no removal of cut bone or tissue.

U.S. Pat. No. 4,589,414 shows a surgical cutting instrument with a reciprocatory cutting motion, but which has no removal of cut bone or tissue, and no flexibility in the instrument.

U.S. Pat. No. 4,603,694 shows a rotating arthroscopic shaver with suction, but which is not flexible and which has no removal of cut bone or tissue.

U.S. Pat. No. 4,751,922 shows a flexible medullary reamer with a plastic shaft and a guide rod, but which has no suction and no removal of the cut bone or tissue.

U.S. Pat. Nos. 4,798,213, 4,649,918, and 4,142,517 show various apparatus for bone coring.

SUMMARY OF THE INVENTION

The present invention is a percutaneous tissue removal apparatus including a flexible drill shaft and means for transmitting motion to the shaft. A cutting tip is mounted on the shaft to cut tissue fragments from the tissue. The tissue fragments are removed by suction along the flexible drill shaft to a location outside the body while cutting. One or more selected components of the removed tissue fragments may be collected for implantation, preferably into the body of the patient from whom they were removed. Because the drill shaft is flexible, the surgeon can guide the cutting tip into various locations within the tissue from a small (percutaneous) incision. The surgeon can cut around arcs or angles, rather than only being able to go in a straight line, to reach any desired location, and to avoid vital tissue which would otherwise be in the cutting path. For example, when removing unwanted tissue inside a knee joint the drill shaft can deform, and is therefore less likely to damage normal tissue or joint surfaces. None of these functions is possible with a straight line system.

GENERAL DESCRIPTION OF THE INVENTION

The present invention is a percutaneous tissue removal device and method. In the preferred embodiments described below, the apparatus and method are illustrated as used for removal of bone tissue, but such description is for illustrative purposes only. The invention is not limited to the removal of bone tissue and may be used for removal of cartilage, muscle, fetal tissue, etc. It may be used to break up and remove kidney stones, in the gall bladder for a stone or tumor, in the stomach, in the colon to remove a polyp or tumor, etc. It can reach spaces not currently available with the straight line systems currently available.

A percutaneous tissue removal apparatus in accordance with the present invention includes a flexible drill shaft for insertion inside a tissue. A cutting tip is mounted on the drill shaft for cutting the tissue. Either rotating motion or reciprocating motion is transmitted to the drill shaft to move the cutting tip against the tissue to cut tissue fragments from the tissue. While cutting, the tissue fragments are removed by suction to a location outside the body. The drill shaft and cutting tip are small enough to be usable percutaneously. They may also be used for endoscopic, arthroscopic or fiberoptic or open surgery.

Because the drill shaft is flexible, the surgeon can guide the cutting tip into various locations within the tissue from one percutaneous incision. The surgeon can cut around arcs or angles, rather than only being able to go in a straight line, to reach any desired location, and to avoid vital tissue which would otherwise be in the cutting path. The flexible drill shaft also allows the surgeon when working inside a bone, for example, to keep the cutting tip away from the harder outer cortical bone and to remove only the softer inner cancellous bone. None of these features is available with the current straight line cutting devices.

The drill shaft may be made of metal, of polymeric material to reduce friction, or of a composite material. Extensive use of polymers in the drill shaft, its housing if provided, and the cutting tip area reduces friction substantially, thus requiring less energy and generating less heat within the tissue. The drill shaft is drivable by hand (for improved feel) or by motor, at variable speeds based on the need for the tissue removed.

To provide for the collection of the tissue fragments to be harvested, the removal apparatus has an axially extending suction passage along the drill shaft through which the tissue fragments are removed. The suction passage has a smooth lining to keep the tissue fragments or graft material contained and to reduce friction of the harvested tissue fragments. This lining may be the inside diameter of the flexible drill shaft itself, or may be a separate liner sleeve which can be removed and disposed of when it becomes unsanitary or clogged, without having to remove the drill shaft and cutting tip. Alternatively, if a separate guide sleeve or guide rod is used the suction passage may be formed between the drill shaft and the guide sleeve or guide rod. In such a case, the drill shaft may be solid rather than hollow.

The cutting tip is made of a material which is harder than the material to be cut. The cutting tip may be slightly larger in diameter than the drill shaft. The cutting tip may be made of a polymeric material or a composite material. Alternatively, the cutting tip may be made of a ceramic material. The cutting tip is separable from the drill shaft, and several different cutting tips may be provided in varying hardnesses, so that the surgeon can selectively remove various portions of tissue as desired.

By virtue of its flexibility, the flexible drill shaft, when removing bone tissue, may stay within the cortical confines of the bone. Alternatively, it may work with a guide device to control the location of the cutting tip within the bone. The guide means may be a guide rod extending within the flexible drill shaft, or a hollow guide sleeve outside the flexible drill shaft. The guide rod or guide sleeve may be rigid in a particular shape, to fit a particular application; or it may be bendable into a particular shape which it will hold; or it may be selectively rigidifiable into a particular shape in situ. The guide means may include structure for positioning the tip of the flexible drill shaft. The guide means may also be inserted into a separate flexible tube system to guide it to a specific location, then removed, allowing the flexible drill to be inserted.

Fluid may be injected through the flexible drill shaft to a location adjacent the cutting tip to increase the efficiency of the tissue removal and to limit thermal necrosis. Alternatively, a fluid injection passage may extend axially along the flexible drill shaft, the drill shaft. Alternatively, fluid may be injected through the suction passage, alternating with the suction. The fluid injection may be constant or it may be pulsatile in nature. If fluid injection is used, centrifuging of the harvested material may be performed.

Means for collecting one or more selected components of the harvested tissue fragments may include a known trap or filter connected to the outlet of the suction passage. Removed tissue may be centrifuged to separate its components. Thus, the tissue fragments are not merely removed from the body and may be harvested for implantation of the fragments, preferably into the body of the patient from whom they were removed. In order to maintain the sterility of the tissue removed, the entire suction apparatus including the suction passage and the trap or filter is sterilized, and, if necessary, is disposable.

With the present invention all work is done by going percutaneously through the skin to a specific tissue area to minimize the damage to skin, muscle, and bone. For example, when removing bone tissue, trauma is limited to a small opening in the hard outer structural cortical bone, limiting postoperative bleeding from the bone which is difficult to stop, because the small operative hole can easily be plugged after the grafting procedure is completed, preventing postoperative bleeding into soft tissue. There is only intraosseous bleeding, so that fewer complications, and less pain, are likely to arise. The operation does not create stress risers which would weaken the bone. Thus, the present invention provides a safe and efficient way to collect and reuse a patient's own tissue.

Human tissue grafting works best using the patient's own tissue as donor material. Therefore, the harvested tissue may be implanted in the donor's own body for grafting. To implant one or more selected components of harvested bone fragments, for example, a cannula is inserted through the skin and muscle to the area of the bone where the graft is to be placed. A drill or curette is then used to remove a portion of the outer cortical bone. A curette or probe is inserted through the cannula to clear out the area where the graft is to be placed, either in open surgery or through X-ray guidance in percutaneous surgery. The harvested tissue fragments may be packed or compressed into a plug of tissue graft material, of a specific shape, with or without blood or fibrin for adhesion. Or, a retaining material such as a biodegradable mesh may be used to hold the graft material together as a unit. The graft material and its retaining material are then inserted at the graft location in the bone. Alternatively, the graft material is inserted and then sealed in place with a mass of formable polymeric material inserted over the graft material to hold the graft together in position.

A method of percutaneous tissue removal in accordance with the present invention includes the steps of placing within a tissue mass a flexible drill shaft having mounted thereon a cutting tip for cutting the tissue; transmitting motion to the drill shaft to move the cutting tip against the tissue to cut tissue fragments from the tissue; and removing the tissue fragments by suction to a location outside the tissue mass while cutting the tissue. The method may further include the step of controlling the location of the cutting tip within the tissue with a guide rod, the step of collecting one or more selected components of the harvested tissue fragments, and/or the step of implanting the fragments into the body of the patient from whom they were removed.

BRIEF DESCRIPTION OF THE INVENTION

Further features of the present invention will become apparent to those skilled in the art to which the present invention relates from reading the following specification with reference to the accompanying drawings, in which:

FIG. 8 illustrates a portion of a flexible drill including a solid formable inner guide rod within a flexible outer cutting sleeve and a suction passage between;

FIG. 9 illustrates a portion of a flexible drill including a hollow flexible inner cutting shaft within a solid formable outer sleeve and a suction passage between;

FIG. 11 illustrates a portion of a flexible drill including a solid flexible inner cutting shaft within a solid formable outer sleeve and a suction passage between;

FIG. 12 illustrates a portion of a flexible drill including a relatively flexible portion between two relatively rigid portions;

FIG. 13 illustrates the use of a liner sleeve in a suction passage;

FIG. 14 is a view illustrating a number of different cutting tips usable with the flexible drill;

FIGS. 15 and 16 are schematic views illustrating the provision of a plurality-y of separately inflatable bladders as a guide mechanism for a flexible structure and the operation of a guidance system for locating the tip of the flexible structure;

FIGS. 17A and 17B are schematic views illustrating the forming of harvested tissue fragments into a compressed plug suitable for implantation;

FIG. 18 is a schematic view illustrating the implantation of harvested bone fragments using a polymeric mesh as a retainer; and FIGS. 19A and 19B are schematic views illustrating the implantation of harvested tissue fragments using a formable polymeric sealant as a retainer.

DETAILED DESCRIPTION OF THE INVENTION

The present invention is described herein with reference to a percutaneous bone removal and harvesting apparatus and method. It should be understood that the present invention is not limited to the removal of bone tissue, but is useful in the removal of any hard or soft tissue in the body such as excess, unwanted, or tumorous tissue or tissue used for reimplantation or grafting.

Figure 1:
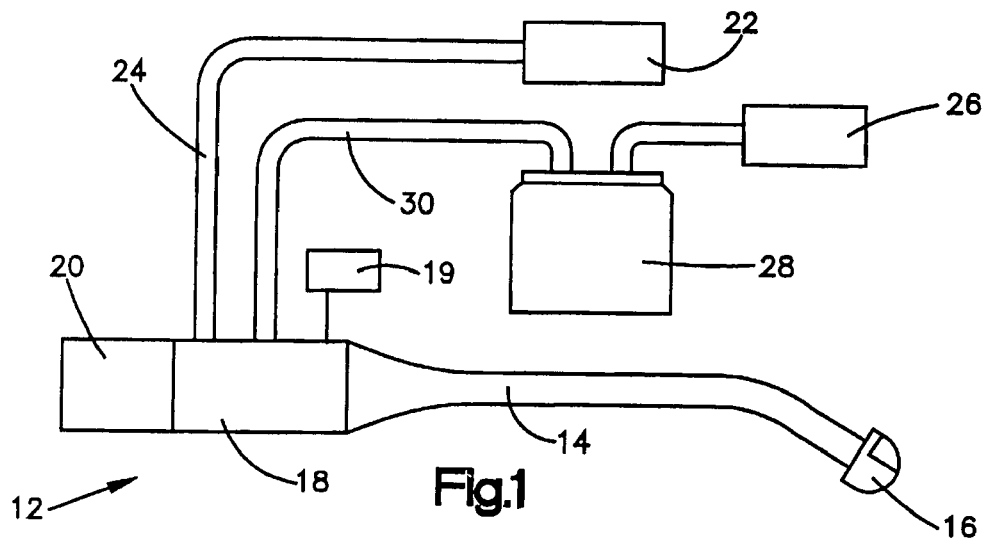
FIG. 1 is a schematic view of a tissue removal system in accordance with the present invention and including a flexible drill.

A percutaneous bone removal apparatus 10 (FIG. 1) in accordance with the present invention includes a flexible drill 12. The flexible drill 12 has a flexible shaft 14 and a cutting tip 16 at the distal end of the shaft 14. The proximal end of the flexible shaft 14 is connected by a housing 18 to a motor or other power source 20 to provide rotational motion or reciprocating motion in a manner known in the art. Alternatively, the drill 12 may have an angled drive, such as 90.degree. drive or any angle, with the motor drive connected at an angle to the longitudinal extent of the suction and cutting apparatus.

Control means indicated schematically at 21 may include one or more switches or valves to turn on or off the suction, irrigation, and motor drive. control A fluid injection source 22 is connected by a fluid injection line 24 to the housing 18 of the flexible drill 12. A suction source 26 acts through a trap or filter or strainer 28 and a suction line 30 to provide suction capabilities for the flexible drill 12.

Figure 2:
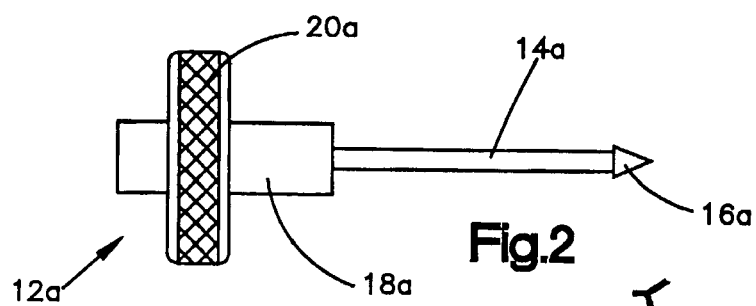
FIG. 2 is a schematic view of a hand-powered flexible drill for use in the system of FIG. 1.

FIG. 2 illustrates a flexible drill 12a in which the housing 18a is connected to a hand controller 20a. The hand controller 20a allows the surgeon to operate the flexible drill 12a by hand, imparting either rotational or reciprocating movement to the flexible shaft 14a and cutting tip 16a.

Figure 3:
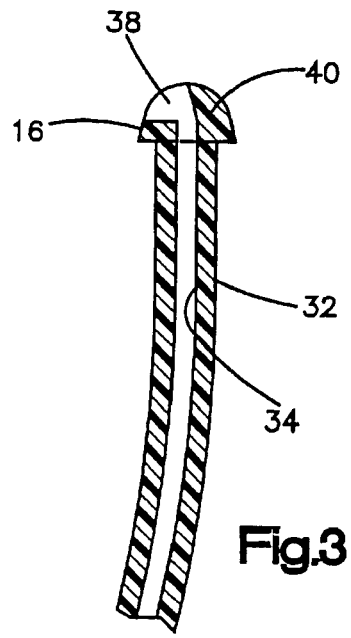
FIG. 3 is a schematic view of a portion of a hollow flexible drive shaft for the flexible drill.

FIG. 3 illustrates a portion of a basic version of a flexible drill having a cutting tip 16 mounted on a flexible drive shaft 31. The drive shaft 31 has an outer surface 32 and an inner surface 34 defining a longitudinally extending suction passage 36. The cutting tip 16 has a cutting edge 40 and an opening 38 through which tissue fragments cut by the cutting tip 16 may be aspirated. The tissue fragments are drawn through the suction passage 36 in the flexible drive shaft 31 and thence into the suction line 30 (FIG. 1) for collection in the trap or filter or strainer 28.

Figure 4:
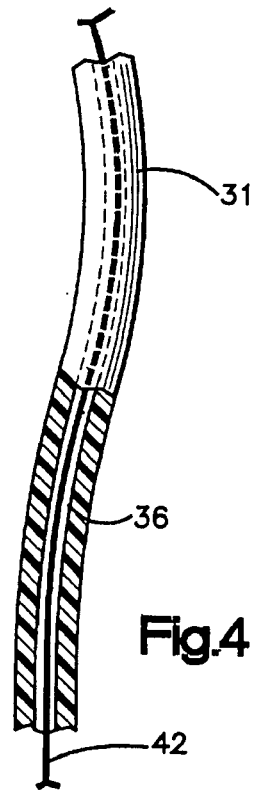
FIG. 4 is a schematic view similar to FIG. 3 and showing a guide rod inside the hollow flexible drive shaft.

FIG. 4 illustrates the use of a pre-inserted guide rod 42 with a flexible drill of the present invention. The guide rod 42 extends through the suction passage 36 of the flexible drive shaft 31. The guide rod 42 may be any suitable structure including a K-wire or other known device. The cutting tip 16 may have a centrally located opening in its distal end to allow insertion of the flexible drill over the guide rod 42. The guide rod 42 is first placed in the body, then the flexible drill is inserted over the guide rod 42 and guided to the location from which tissue is to be harvested.

Figure 5:
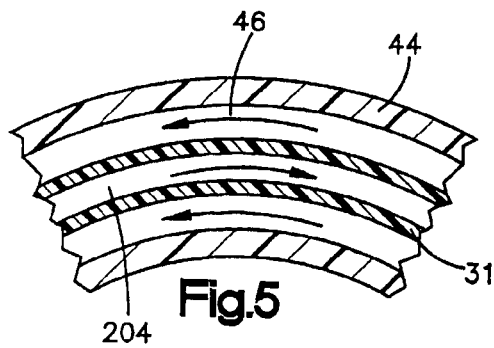
FIG. 5 illustrates a portion of a flexible drill including a hollow flexible inner cutting shaft within a flexible outer sleeve and a suction passage between the two shafts.
Figure 6:
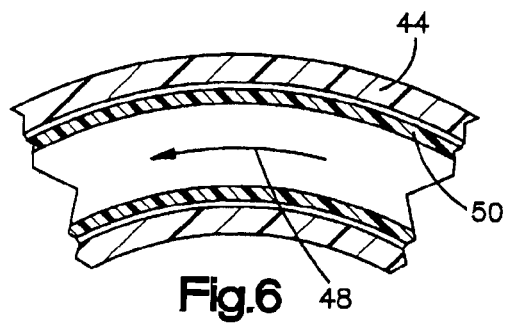
FIG. 6 is a view similar to FIG. 5 with a suction passage within the inner shaft.

FIG. 5 illustrates an embodiment of a flexible drill having an outer sleeve 44 circumscribing a flexible drill shaft 41. The flexible outer sleeve 44 may be formed of a metal or composite material or may be formed of a polymeric material which may be the same as or different from the material of the flexible inner cutting shaft 31. The outer sleeve 44 is fixed (non-moving) to minimize tissue damage. A suction passage 46 is defined between the outer surface of the flexible inner shaft 31 to which the cutting tip is attached, and the inner surface of the flexible outer sleeve 44. Alternatively, as shown in FIG. 6, a suction passage 48 may be defined within the flexible inner cutting shaft 50. In this case, the outer surface of the flexible inner shaft 50 is preferably, as illustrated in FIG. 6, in close proximity to the inner surface of the outer sleeve 44 to increase stability. The use of polymeric materials for both the inner shaft 50 and the outer sleeve 44 provides for reduced friction between the sleeve 44 and the shaft 50 for ease of operation and reduced heat generation.

Figure 7:
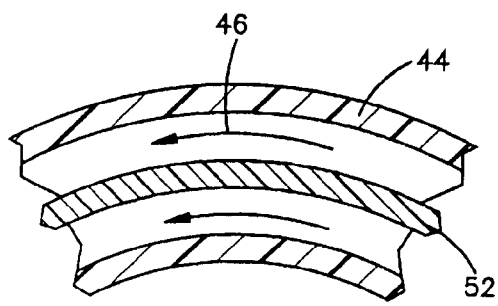
FIG. 7 illustrates a portion of a flexible drill including a solid flexible inner cutting shaft within a flexible outer sleeve and a suction passage between the two shafts.

FIG. 7 illustrates an alternate embodiment of the apparatus of FIG. 5 in which the flexible inner cutting shaft 52 is formed as a solid shaft rather than a hollow shaft. The harvested tissue fragments travel through the suction passage 46 between the inner shaft 52 and the outer sleeve 44.

Figure 8:
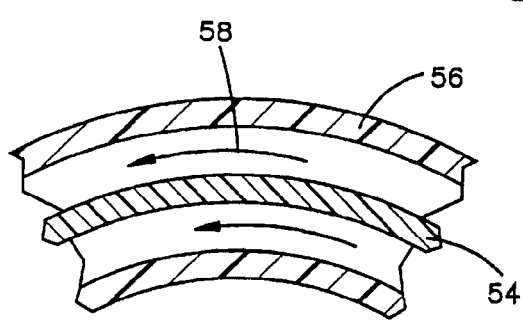

FIG. 8 illustrates apparatus similar to FIG. 7 in which a fixed (non-moving) inner shaft 54 is made of a solid, formable, material and the cutting tip is mounted on a flexible rotating outer sleeve 56. Suction is drawn through a suction passage 58 between the shaft 54 and the sleeve 56. The inner shaft 54 is made from a semi-rigid material which is bendable to a desired curvature, at the use site, to select the curvature of the hole to be drilled, and which is rigid enough to retain that curvature in use while the drill shaft 56 rotates around it. Such material is disclosed in U.S. Pat. No. 4,541,423, the disclosure of which is incorporated herein by reference.

Figure 9:
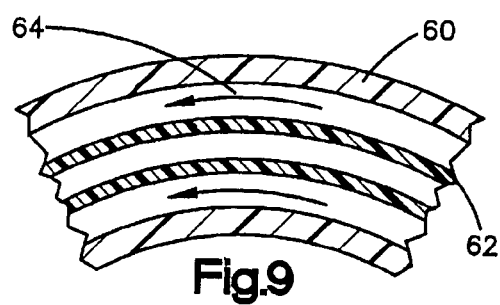
Figure 10:
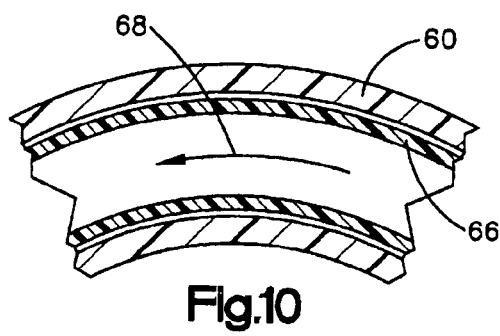
FIG. 10 is a view similar to FIG. 9 with a suction passage within the inner shaft.
Figure 11:
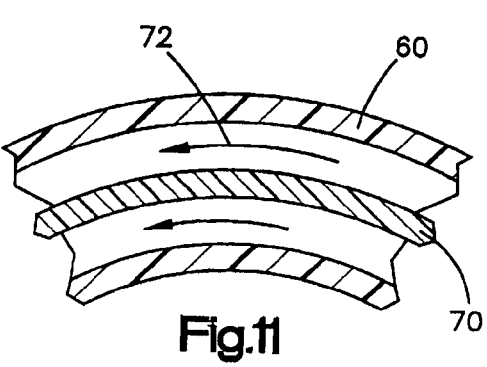

FIGS. 9, 10 and 11 illustrate embodiments of the flexible drill of the present invention in which a flexible inner cutting shaft, which may be hollow or solid, is disposed within a non-moving formable outer sleeve. The formable outer sleeve 60 is made of a semi-rigid bendable shape retaining material as described above with reference to FIG. 8. In FIG. 9, a hollow flexible inner cutting shaft 62 is disposed within the outer sleeve 60 and defines therebetween a suction passage 64. In FIG. 10, a hollow flexible inner cutting shaft 66 is disposed in close proximity to and within the outer sleeve 60, with a suction passage 68 formed within the flexible inner cutting shaft 66. In FIG. 11, a solid flexible inner cutting shaft 70 is disposed within the outer sleeve 60, defining therebetween a suction passage 72.

FIG. 12 illustrates a portion of a flexible drill shaft 80 in accordance with the present invention in which a pair of relatively rigid drill portions 82 and 84 are joined by a relatively flexible drill portion 86. The relatively rigid drill portion 82 includes an outer sleeve 88, an inner shaft 90, and a suction passage 92 therebetween. The relatively rigid drill portion 84 includes an outer sleeve 94 like the outer sleeve 88, an inner shaft 96 like the inner shaft 90, and a suction passage 98 therebetween. The drill portion 86 includes a relatively flexible inner shaft portion 100 disposed within a relatively flexible outer sleeve portion 102, defining therebetween a suction passage 104. The relatively flexible inner shaft portion 100 connects the relatively rigid inner shaft portions 90 and 96. The relatively flexible outer sleeve portion 102 connects the relatively rigid outer sleeve portions 88 and 94. The suction passage 104 in the relatively flexible drill shaft portion 86 connects the suction passages 92 and 98. Either the inner shaft or the outer sleeve of the flexible drill 80 may have a cutting tip mounted thereon. Thus, with a flexible drill shaft made in this manner, it is not necessary that the entire drill shaft be made of flexible materials, but rather "joints" such as are formed by the relatively flexible portion 86 may be placed along the longitudinal extent of a relatively rigid drill shaft as desired.

FIG. 13 illustrates how a disposable single-use liner sleeve 110 may be used in a flexible drill of the present invention. The liner sleeve 110 shown in FIG. 13 is located within an outer sleeve 112 and is shown about a guide rod or guide wire 114. Suction is drawn through a passage 116 within the liner sleeve 110. The disposable single-use liner sleeve 110 provides an absolutely sterile environment through which harvested tissue fragments may pass. The inner surface 118 of the liner sleeve 110 is extremely smooth in order to facilitate passage of the harvested tissue fragments therethrough. It should be understood that a liner sleeve like the liner sleeve 110 may be used with any suitable flexible drill shaft configuration in accordance with the present invention, and not merely with the configuration shown in FIG. 13.

FIG. 14 illustrates several different cutting tips which may be attached in a known manner to a flexible drill shaft in accordance with the present invention. The technology for the cutting tips is not specific to the present invention, but rather the cutting tips may be designed in accordance with known principles.

The cutting tip 120 (FIG. 14) has a cutting edge 122 at least partially defining an opening 123 through which suction is drawn. The cutting tip 124 includes a plurality of cutting edges 126 defining a plurality of suction openings 128 disposed along the outer circumferential portion of the cutting tip 124. The cutting tip 130 is similar to the cutting tip 124 but includes cutting edges 126a and suction openings 128a which extend to the end of the cutting tip 130. Furthermore, the cutting tip 130 is blunt rather than sharp, to avoid perforation of tissue, such as bones.

The cutting tip 132 has a spiral cutting edge 134 defining a spiral suction opening 136. The cutting tip 138 has at least one longitudinally extending cutting edge 140 at least partially defining a longitudinally extending suction opening 142. The cutting tip 143 is formed as a burr with fluted cutting edges 144 and suction openings 145, and is especially suited for shaving operations such as removal of bone spurs, etc. The cutting tip 146 has twin cutting edges 147 and 148 and a suction opening 149. The cutting edges 157 and 148 can be configured with the leading edge to grab the tissue and the trailing edge to cut the tissue.

The configuration of a cutting tip for use in accordance with the present invention is a design choice within the skill of the art. The goals to be met are proper cutting and suction capabilities, controllability and shape so as to avoid unwanted damage to areas of tissue not to be cut. For example, when removing the softer cancellous portion of bone, the cutting tip may be made of a material which is harder than the cancellous material of the bone but softer than the cortical portion of the bone to avoid damage thereto. Metal may be useful, and suitable polymers are also readily available. Ceramic materials and composites are also suitable. Also, the cutting tip may be arranged as a rotating flexible shaft within a fixed flexible outer shaft, with a cutting edge on the rotating shaft to cut tissue off against the fixed edge. In such a case, the apparatus may be advantageously configured with one shaft being metal and the other polymeric, to minimize friction and heat buildup.

FIGS. 15 and 16 illustrate an alternate guidance system for positioning a flexible drill shaft 152 and its associated cutting tip. Disposed within the sleeve 150 is a guidance mechanism 152 including a plurality of inflatable elements spaced serially. The inflatable elements, when inflated, rigidify and become straight, while when in the deflated condition they are soft and flexible and may be curved or bent. Thus, as seen in FIG. 15, both the inflatable elements designated 154 and the inflatable elements 156 are curved. In FIG. 16, the inflatable elements 154 have rigidified and straightened, while the inflatable elements 156 remain in their curved position. The inflatable elements may also be accordion shaped, expanding in length as they are inflated. The mechanism 152 may be augmented with a known cable guidance system.

By selectively and individually controlling the rigidification of any or all of the inflatable elements of the mechanism 152, the inflatable mechanism 152 and its associated outer sleeve 150 may be selectively formed into almost any desired shape or position. Suitable control and valving apparatus is provided for controlling the inflation of the inflatable elements. Such apparatus may be, when only a few elements are present, a simple mechanical valving apparatus. When more elements are present, or more sophisticated or complex control thereof is desired, a microprocessor may be used to control the inflation of each segment. Separate inflation and deflation lines can be used, or one line can, by alternating valving, serve both functions. In such case, the control signals may be multiplexed down the structure via electric wire, optical fiber, or radio control, for example.

At the distal end of the mechanism 152 is a tip guidance mechanism 160 including a plurality of inflatable members 162. The inflatable members 162 when in a deflated condition are flexible and relatively straight. When inflated, as shown in FIG. 16, the members 162 assume a preformed shape which may be curved or straight and which is illustrated herein as a curved shape, bending radially outwardly to engage the surface of adjacent tissue 164 and curve the end of the device into an appropriate position. The members 162 may be constructed, using known principles, to assume any desired shape. By controlling the positioning of one or more of the elements 162, the tip portion 168 of the guidance mechanism 152 may be selectively placed in any position relative to the tissue 164, thus positioning the end of the sleeve 150. The air bladder guidance system as described may be used in conjunction with a flexible tube separate from the flexible drill shaft, order to guide the flexible tube to a specific location and position it there, thereafter removing the guidance system and allowing a flexible drill to be inserted.

Means for collecting one or more selected components of the harvested tissue fragments includes a mechanism 28 (FIG. 1) which may be a known trap or filter connected to the outlet of the suction passage 30. Removed tissue may also be centrifuged if necessary or desired, keeping the components such as bone, cells, and blood and discarding fluid. These components and connections, and their uses, are well known in the art and thus are not described herein in greater detail. The harvested tissue fragments are not merely removed from the body of the patient, but are also collected in the structure 28 and thus harvested or saved for later implantation of the fragments, preferably into the body of the patient from whom they were removed. Such harvesting and implantation are desirable because human tissue grafting works best using the patient's own tissue as donor material.

In preparing the harvested graft material for implantation, the tissue fragments alone are spun or compressed (see FIG. 17B) to form them into the desired shape. When the tissue is harvested, blood and blood clots are often drawn along with the tissue fragments. The blood component fibrin is a sticky clotting component, and can be used to aid in holding the tissue fragments together for implantation. Thus, the blood can be is separated from the tissue fragments and then spun to separate the fibrin for use with the tissue fragments. Alternatively, the entire mass of tissue fragments and blood is compressed into a specific shape to form the mass into a specific, appropriate shape for implantation into the body.

The surgeon can also place other substances into the graft material to be implanted, such as other tissue graft material, collagen, antibiotics, or ceramic hydroxyapatite or tricalcium phosphate to aid in bone ingrowth. In such a case, when the blood or fibrin is used also, the graft has the adhesive qualities of the blood or fibrin and the biological properties of the bone (or other) tissue, along with the appropriate medical properties of any other material included.

Harvested tissue fragments before implantation are preferably packed or compressed into a plug of tissue graft material. Alternatively, the tissue fragments may be left in a more loose state, or only certain selected cells, components, or tissue fragments are used. Any suitable means of packing or compressing fragments may be used. FIGS. 17A and 17B illustrate schematically a simple apparatus for doing so. As viewed in FIGS. 17A and 17B, the harvested tissue pieces 170 are placed into a form or mold 172 and then compressed by a movable compressor 174 to form a plug 176 of a desired shape or size. Unwanted fluid drains out through one or more fluid outlets 178, while the graft, cells, fibrin, and blood clot tissues remain within the form 172.

To implant one or more selected components of the harvested tissue fragments, for example in grafting bone tissue onto a bone, a cannula 180 is inserted through the skin 182 and muscle 184 to the area of the bone 186 where the graft is to be placed. A curette or probe is then inserted through the cannula 182 to clear out the area 188 where the graft is to be placed.

The harvested tissue fragments are compacted or compressed into a plug 190 of tissue graft material. A retaining material such as a known biodegradable or other polymeric mesh 192 is then used to hold the graft material 190 together as a unit. The retaining material may also be a sac of biodegradable material used to hold the graft material. The sac can be closed by a clamp or by crimping or heat sealing. The graft material 190 and its retaining material 192 are then inserted into the graft area of the bone. The cannula 180 may then be removed. Alternatively, the tissue graft material may be held in place by a mass of biodegradable or other polymeric material used as a sealant for the opening in the bone 186. The graft material can be compressed or spun into a specific shape. Thus, if an implant is needed to fit a specific shape of bone defect, the graft material can be formed in the shape needed and packed directly into the bone gap.

The bone graft material may also be implanted in the loose condition as described above. The bone graft material 194, if loose, can be inserted through a funnel 196 and a sleeve 198 located within the cannula 180 to the area 188 to be grafted. It is then packed in place as desired using a suitable instrument. Next, an injector 200 is used to inject a mass of flowable biodegradable or other polymeric material 202 for use as a sealant to seal the bone graft material 194 in position. The use of a flowable biodegradable material is preferable in that it allows the surgeon to form in situ a custom shaped sealant plug to seal the opening in the tissue graft area, which will eventually resorb as new tissue grows into its place.

The apparatus may include, as noted above, fluid injection means 22 and 24 for injecting fluid through the flexible drill to a location adjacent the cutting tip to aid in cutting and removal of the harvested tissue fragments. For example, in the drill shaft structure illustrated in FIG. 5, fluid may be injected through a fluid injection passage 204 within the flexible inner cutting shaft 31, while suction is drawn in the opposite direction through the suction passage 46. Alternatively, the suction may be intermittently discontinued and fluid may be injected through the suction passage, alternating with the suction. The fluid injection may be constant or it may be pulsatile in nature.

The present invention thus provides a method of percutaneous tissue removal which includes the steps of placing adjacent to a tissue mass a flexible drill shaft 14 having mounted thereon a cutting tip 16 for cutting the tissue; transmitting motion to the drill shaft 14 to move the cutting tip 16 against the tissue to cut tissue fragments from the tissue; and removing the tissue fragments by suction to a location outside the tissue mass while cutting the tissue. The method may further include the step of controlling the location of the cutting tip within the tissue with a guide mechanism, the step of collecting one or more selected components of the harvested tissue fragments, and/or the step of implanting the fragments into the body of the patient from whom they were removed.

From the above description of the invention, those skilled in the art will perceive improvements, changes and modifications. Such improvements, changes and modifications within the skill of the art are intended to be covered by the appended claims.

The invention claimed is:

1. A method for processing cells implantable in a recipient for therapeutic use, the method comprising the steps of:
   harvesting tissue fragments from a plurality of locations within a tissue of a donor from one percutaneous incision;
   separating cells from the tissue fragments; and
   placing the cells in a form until implantation,
   wherein the tissue fragments contain cartilage tissue and the cells are viable.

2. The method of claim 1 wherein the donor and recipient are the same individual.

3. The method of claim 1 wherein the donor and recipient are different individuals.

4. The method of claim 1 wherein the cells are at least partially separated using a filter.

5. The method of claim 1 wherein the cells are at least partially separated using centrifugation.

6. The method of claim 1 wherein the cells are at least partially separated using a press.

7. The method of claim 1 wherein the cells are at least partially separated using a filter and centrifugation.

8. The method of claim 1 wherein prior to implantation the cells are combined with a material selected from the group consisting of tissue grafts, collagen, antibiotics, and bone growth promoting substances.

9. The method of claim 8 wherein the bone growth promoting substances are hydroxyapatite or tricalcium phosphate.

10. The method of claim 1 wherein an adhesive element is added to the cells.

11. The method of claim 10 wherein the adhesive element is blood or fibrin.

12. The method of claim 1 further comprising the step of adding the cells to a biodegradable material.

13. The method of claim 1 further comprising the step of adding the cells to a polymer.

14. The method of claim 1 wherein the cells include at least two cell types.

15. The method of claim 1 wherein the cells are formed into an implant prior to implantation into the recipient.

16. A method for processing cells to be implanted in a recipient for therapeutic use, the method comprising the steps of:

harvesting tissue fragments from a plurality of locations within a tissue of a donor from one percutaneous incision;

separating cells from the tissue fragments; and combining the cells with a material selected from the group consisting of tissue grafts, collagen, antibiotics, and bone growth promoting substances, wherein the cells are viable and tissue fragments contain tissue selected from the group consisting of bone, cartilage, muscle, and fetal tissue.

17. The method of claim 16 wherein the donor and recipient are the same individual.

18. The method of claim 16 wherein the donor and recipient are different individuals.

19. The method of claim 16 wherein the cells are placed in a form prior to implantation.

* * * * *